United States Patent
Mohebbi et al.

(10) Patent No.: US 10,896,244 B2
(45) Date of Patent: *Jan. 19, 2021

(54) MEDICATION MONITORING AND IDENTIFICATION

(71) Applicant: GoodRx, Inc., San Francisco, CA (US)

(72) Inventors: Matthew Mohebbi, San Francisco, CA (US); Thomas Goetz, San Francisco, CA (US)

(73) Assignee: GOODRX, INC., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/720,020

(22) Filed: Dec. 19, 2019

(65) Prior Publication Data

US 2020/0135331 A1    Apr. 30, 2020

Related U.S. Application Data

(63) Continuation of application No. 14/535,062, filed on Nov. 6, 2014, now Pat. No. 10,552,575.

(60) Provisional application No. 61/901,337, filed on Nov. 7, 2013.

(51) Int. Cl.
| | | |
|---|---|---|
| *G16H 20/10* | (2018.01) | |
| *G06F 19/00* | (2018.01) | |
| *G06K 9/46* | (2006.01) | |
| *G06K 9/62* | (2006.01) | |
| *G16H 30/40* | (2018.01) | |

(52) U.S. Cl.
CPC ........ *G06F 19/326* (2013.01); *G06F 19/3456* (2013.01); *G06K 9/4609* (2013.01); *G06K 9/6202* (2013.01); *G16H 20/10* (2018.01); *G16H 30/40* (2018.01)

(58) Field of Classification Search
None
See application file for complete search history.

(56) References Cited

U.S. PATENT DOCUMENTS

| | | |
|---|---|---|
| 6,535,637 B1 | 3/2003 | Wootton et al. |
| 9,852,261 B1 | 12/2017 | Havard et al. |
| 2003/0144874 A1 | 7/2003 | Barret et al. |

(Continued)

OTHER PUBLICATIONS

"DrugDigest Alerts Consumers about Mixing Medications with Herbal Supplements." Business Wire, Nov. 6, 2003, p. 5528. ProQuest. Web. Sep. 18, 2019 . (Year: 2003).*

(Continued)

*Primary Examiner* — Lena Najarian
(74) *Attorney, Agent, or Firm* — Fenwick & West LLP

(57) ABSTRACT

A medical monitoring system extracts characteristic information for one or more medications from an image of the one or more medications on an uncontrolled background, the image being taken by a client device associated with a user of the medical monitoring system. The medical monitoring system determines prescription information associated with a medication, of the one or more medications, using the extracted characteristic information and a medication database, the medication database containing mappings between prescription information and characteristic information for a plurality of medications. The medical monitoring system provides a portion of the prescription information to the client device.

20 Claims, 11 Drawing Sheets

(56) References Cited

U.S. PATENT DOCUMENTS

2003/0200726 A1  10/2003  Rast
2006/0247968 A1  11/2006  Kadry
2010/0312578 A1  12/2010  Hardaway
2011/0082867 A1  4/2011  Bruns et al.
2011/0119073 A1  5/2011  Hanina et al.

OTHER PUBLICATIONS

Business Wire, "DrugDigest Alerts Consumers about Mixing Medications with Herbal Supplements," Nov. 6, 2003, pp. 5528.
United States Office Action, U.S. Appl. No. 14/535,062, dated Jun. 6, 2019, 14 pages.
United States Office Action, U.S. Appl. No. 14/535,062, dated Nov. 27, 2018, 17 pages.
United States Office Action, U.S. Appl. No. 14/535,062, dated May 23, 2018, 16 pages.
United States Office Action, U.S. Appl. No. 14/535,062, dated Nov. 28, 2017, 12 pages.

* cited by examiner

MEDICATION MONITORING AND IDENTIFICATION

CROSS-REFERENCE TO RELATED APPLICATIONS

This application is a continuation of U.S. patent application Ser. No. 14/535,062, filed Nov. 6, 2014, allowed, which claims the benefit of U.S. Provisional Application No. 61/901,337, filed Nov. 7, 2013, all of which are incorporated by reference in their entirety.

FIELD OF DISCLOSURE

This disclosure relates to the field of medical monitoring generally, and specifically to facilitating identification of medications and their interaction effects, and consumption of medications at the appropriate time.

DESCRIPTION OF THE RELATED ART

Large sections of the population routinely take medication, and the medication may be prescribed by a doctor or sold to consumers directly without a prescription (i.e., over-the-counter medication). Often the identity of the medication is not apparent from the medication's appearance. Solid oral dosage forms of medication (e.g., tablets, pills, and capsules) are uniquely identified via an imprinted alphanumeric imprint code, however, without additional context, a user typically cannot identify a pill by its imprint code alone. For example, the imprint code for a 5 mg dosage of Oxycodone is M 05 52, and without knowing that M 05 52 corresponds to a 5 mg dosage of Oxycodone, a user would not be able to identify the pill based on looking at the pill itself. This can be problematic since, for example, a pharmacist may accidently fill a prescription with the wrong medication, and the user and/or doctor might not know that the wrong medication was provided to the user.

Additionally, some segments of the population (e.g., elderly or sick) may be taking multiple medications of varying types that are meant to be taken in accordance with a particular schedule. It is not uncommon for a person to be taking different types of medication multiple times a day (e.g., with meals, in the morning, and in the evening, etc.). However, it can be difficult to remember to take the medication at the appropriate time and/or log the taking of the medication.

Moreover, users must be careful to avoid taking medications that would have adverse interaction effects. For example, certain medications when taken in combination can negate the benefits of one or both of the medications, be dangerous to the user, etc. Interaction effects are generally described in a package insert (also known as prescribing information) provided with the prescription medication. A user attempting to determine the interaction effects for multiple pills would have to manually review the often quite long package insert for each of the medications prescribed. Moreover, users typically do not carry around the package inserts for their medication, preventing them from checking to see if their prescribed medications would interact adversely with over-the-counter medications they might want to consume.

SUMMARY

Users are able to identify and track medications taken using a medical monitoring system and method. A client device, such as a mobile phone, is used by a user to take one or more images of medications that are then used to identify the medication, thus allowing the user to confirm that he does in fact have the medication that he is intending to take. The images can be taken with the user's phone or other device on any uncontrolled background, including on a desk, in a user's hand, etc. Certain characteristic information (e.g., the shape, color, size, imprint, etc. can be extracted from the pill(s), and this extraction can occur at a server or medical monitoring system that receives the images taken at the client device, or some or all of the extraction can occur at the client device itself and sent to the medical monitoring system. In some embodiments, the medical monitoring system performs the identification by comparing the images received from the client device to one or more reference images, such as a high resolution photo (e.g., a Food and Drug Administration (FDA) or other government agency or official reference image, such as an SPLIMAGE for oral solid dosage forms submitted to the FDA) and/or a low resolution image (e.g., lower in resolution that the high resolution image, such as one taken by a mobile phone as a reference image). The medical monitoring system can also compare the images or information extracted from the images to reference pill characteristics (e.g., the shape, color, imprint, or size known for different specific pills). The identification of the pill can be provided to the client device. In addition, the invention allows for determining of interactions amongst pills, for tracking current pills being taken for the user (e.g., a digital pillbox), for ordering refills and refill tracking, for logging pills taken by the user and timing for taking the pills, for suggesting alternatives (e.g., alternative treatments, generic medications, etc.), among other functionality.

In one embodiment, characteristic information is extracted for one or more medications from an image of the one or more medications on an uncontrolled background, the image being taken by a client device associated with a user of a medical monitoring system. Prescription information associated with a medication, of the one or more medications, is determined using the extracted characteristic information and a medication database, the medication database containing mappings between prescription information and characteristic information for a plurality of medications. A portion of the prescription information is provided to the client device.

In another embodiment, a selection for medication identification is received on a client device associated with a user of a medical monitoring system. An image is captured of one or more medications on an uncontrolled background using an image capture application. One or more medications are identified using the image, where the identified one or more medications each have associated prescription information, and at least some of the prescription information associated with the identified medication is presented to the user.

In yet another embodiment, an image of one or more medications is received from a client device associated with a user of a medical monitoring system, the image including characteristic information associated with the one or more medications. Characteristic information from the image is extracted, and one or more medications are identified using the extracted characteristic information and a identification database, the identification database containing mappings between prescription information and their associated characteristic information for a plurality of medications. Interaction information associated with the one or more identified medications is determined and then provided to the client device.

In yet another embodiment, an interface is presented to a user of a medical monitoring system via a client device, the interface displaying portions of prescription information for one or more medications. Responsive to receiving a selection to log consumption of a medication associated with the user, a logging interface is presented to the user, the logging interface including a logging option to log the medication as being taken on a medication schedule associated with the user. An image is captured of a medication using an image capture application, and identification information is determined for the medication in the image. The user is prompted to confirm that the determined identification information corresponds to the medication in the image, and responsive to a confirmation received from the user, the medication is logged as being taken.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures and may indicate similar or like functionality.

System Overview

Figure 1:
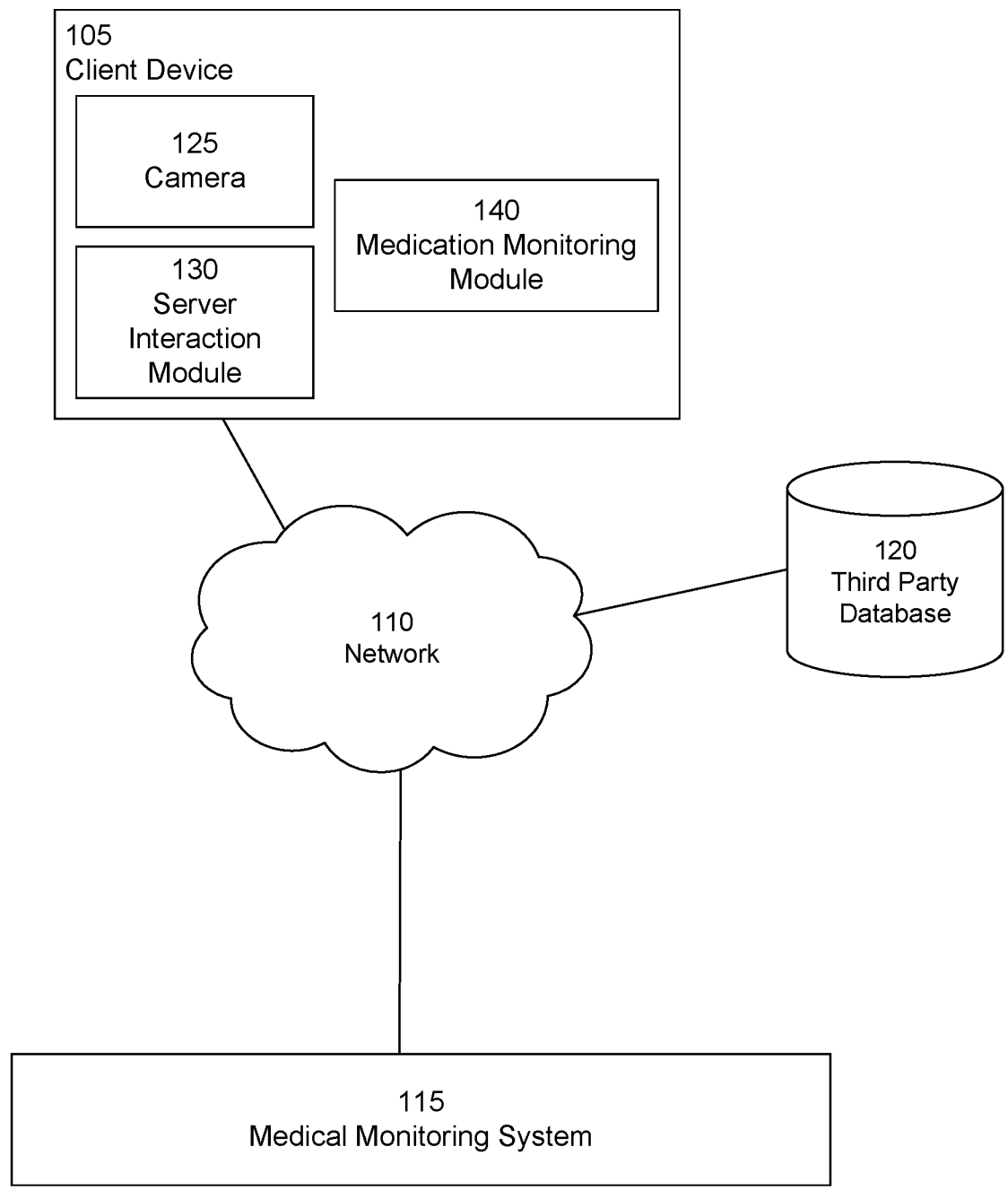
FIG. 1 is a high-level block diagram illustrating an embodiment of a medical monitoring system connected by a network to a client device and a third party database.

FIG. 1 is a high-level block diagram illustrating an embodiment of a medical monitoring system 115 connected by a network 110 to a client device 105 and a third party database 120. Here only one client device 105, third party database 102, and medical monitoring system 115 are illustrated but there may be multiple instances of each of these entities. For example, there may be thousands or millions of client devices 105 in communication with multiple medical monitoring systems 115 and third party databases 120.

The network 110 provides a communication infrastructure between the client device 105, the third party database 120, and the medical monitoring system 115. The network 120 is typically the Internet, but may be any network, including but not limited to a Local Area Network (LAN), a Metropolitan Area Network (MAN), a Wide Area Network (WAN), a mobile wired or wireless network, a private network, or a virtual private network.

The third party database 120 comprises computer servers that host prescription information associated with one or more medications. Prescription information describes medication prescribed by a medical doctor or medication that may be obtained without a prescription (i.e., over-the-counter medication). Prescription information includes clinical pharmacology, indications and usage (i.e., uses/indications for which the drug has been approved by the responsible entity), contraindications (i.e., situations where the medication should not be used), warnings (i.e., possible serious side effects when used alone or with other identified medications), precautions, adverse reactions (i.e., all side effects when used alone or in combination with other medications—including those in the warnings section), drug abuse and dependence (i.e., discusses whether there is a risk of dependence), over dosage (i.e., gives results of overdose and provides recommended actions), dosage and administration (e.g., size of dose and when to take), physical data (e.g., physical characteristics—shape, color, imprint, size, etc.), characteristic information (e.g., information used to identify a medication), a manufacturer of the medication, a brand name of the medication, a generic name of the medication, a description of the medication, an image of the medication (e.g., standard image data), some other information about the medication, or some combination thereof. In some embodiments, the third party database 120 may be controlled by an entity responsible for determining the requirements of package inserts for medication (e.g., in the U.S., this is controlled by the Food and Drug Administration). The third party database 120 may directly provide prescription information to the client device 105 via the network 110, or the third party database 120 may provide prescription information or portions of prescription information to the medical monitoring system 115, and the prescription information may be made available to the client device 105 from the medical monitoring system 115.

The medical monitoring system 115 provides medication information to the client device 105. In some embodiments, the medical monitoring system provides medication information to the client device 105 based on a client request received from the client device 105. Medication information is information associated with a user of the client device 105 and one or more medications. Medication information includes, for example, alerts, vendor information, prescription information, user profile information, interaction information, vendor information, or some combination thereof. In some embodiments, the medical monitoring system 115 generates one or more alerts or instructs the client device 105 to generate and provide an alert to the user.

The client device 105 is a computing device that executes computer program modules which allow a user to utilize the medical monitoring system 115 for medication identification and monitoring. A client device 105 might be, for example, a personal computer, a tablet computer, a smart phone, a laptop computer, GOOGLE® Glass, or other type of network-capable device with imaging capabilities. A client device 105 comprises a camera 125, a server-interaction module 130 and a medication monitoring module 140 in one embodiment. The functions can be distributed among the modules in a different manner than is described here.

The camera 125 is configured to provide imaging capability to the client device 105. The camera 125 digitally captures images. The camera 125 may capture a single image, or series of images. Additionally, in some embodiments, the camera 125 may be configured to capture video. The captured images and/or video may be stored in a local memory. For example, the camera 125 can be used to take an image of one or more pills that a user would like to identify, and the medical monitoring system 115 can provide the identification based on the images. The images used to identify pills can be taken anywhere on any surface or background, such as on a table in the user's home or in the user's hand.

The server interaction module 130 communicates data between the client device 105, the third party database 120, and the medical monitoring system 115, via the network 110. The server-interaction module 130 sends client requests, prescription information, user profile information, or some combination thereof, via the network 110, to the medical monitoring system 115. Additionally, the server-interaction module 130 may receive prescription information from the third party database 120 or the medical monitoring system 115, and medication information from the medical monitoring system 115.

The medical monitoring module 140 is discussed in detail below in conjunction with FIG. 2. The medical monitoring module 140 receives input from the user of the client device 105 to send one or more client requests to the medical monitoring system 115. A client request includes a request type, one or more images of medication adequate for identification, characteristic information associated with one or more of the images of medication, or some subset or combination thereof. Characteristic information is information that may be used to identify a medication. Characteristic information may include, for example, physical data about a medication, or some other information that may be extracted from an image of a medication that may be used to identify that medication. The request type specifies an operation the client request is asking the medical monitoring system 115 to perform. For example, the operation may be to identify one or more medications, identify one or more vendors, determine interaction effects between one or more medications, log consumption of a pill, etc. Additionally, in some embodiments, the medication monitoring module 140 may extract characteristic information from one or more images. The medical monitoring module 140 is configured to perform medication identification, medication tracking, determine medication interaction effects, provide alerts to the user, or some combination thereof, alone or in conjunction with the medical monitoring system 115.

Moreover, the medical monitoring module 140 and/or the medication monitoring system 115 may perform medication identification operations without using a controlled background. A controlled background is a reference background of known, color, size, reflectance, and/or other characteristic, on which objects to be imaged are placed. The use of a controlled background enables easy recognition of objects (less processing needed) placed on the controlled background at the expense of always having to use the controlled background. In contrast, the medical monitoring module 140 and/or the medication monitoring system 115 may identify one or more medications using an uncontrolled background. An uncontrolled background is any background that is not a controlled background. For example, an uncontrolled background may be a piece of paper, a desk, a person's palm, etc. Whereas a controlled background may be, for example, a 3"×4" green card with a one or more reference points, and a specific reflectance. Thus, being able to perform medication identification using uncontrolled backgrounds enables the user to not have to carry with them a controlled background that if lost or damaged would prevent medication identification operations.

The medical monitoring module 140 is configured to present some or all of medication information received from the medical monitoring system 115 to the user. Additionally, the medical monitoring module 140 is configured to allow the user to modify, add, or delete some or all of the medication information and upload the changes to the medication information to the medical monitoring system 115.

Medication Monitoring Module on a Client Device

Figure 2:
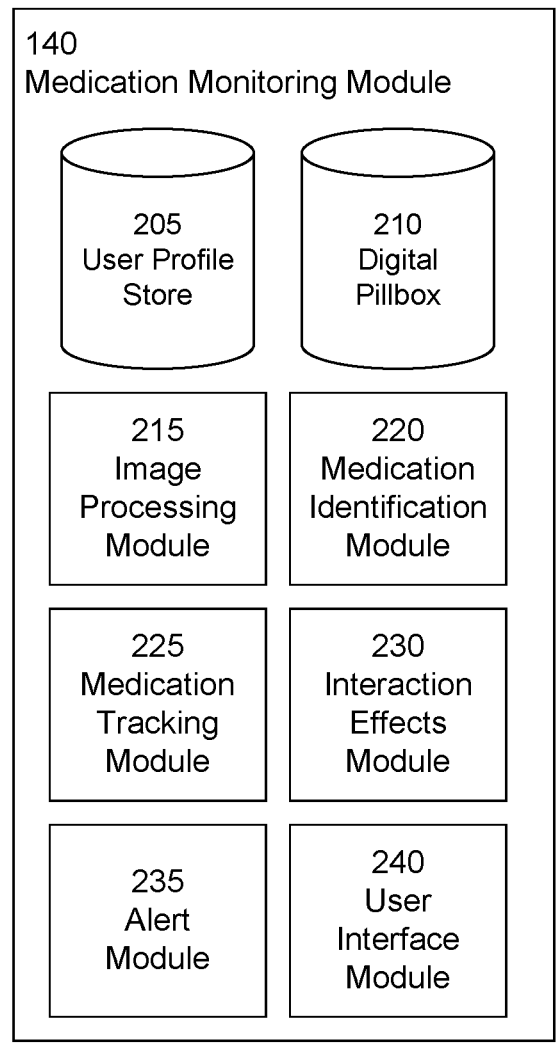
FIG. 2 is a high-level block diagram illustrating a detailed view of the medication monitoring module within a client device according to one embodiment.

FIG. 2 is a high-level block diagram illustrating a detailed view of the medication monitoring module 140 within the client device 105 according to one embodiment. The medication monitoring module 140 is comprised of modules including a user profile store 205, a digital pillbox 210, image processing module 215, a medication identification module 220, a medication tracking module 225, an interaction effects module 230, an alert module 235, and a user interface module 240. Some embodiments of the medication monitoring module 140 have different modules than those described here or may only include a subset of those modules. Similarly, the functions can be distributed among the modules in a different manner than is described here.

Each user of the client device 105 that is also a user of the medical monitoring system 115 is associated with a user profile, which is stored in the user profile store 205. Information stored in the user profile is known as user profile information. A user profile includes declarative information about the user that was explicitly shared by the user and may also include profile information inferred by the medical monitoring system 115. In one embodiment, a user profile includes multiple data fields, each describing one or more attributes of the corresponding user. Examples of information stored in a user profile include login and password information, biographic, demographic, and other types of descriptive information, exercise activity level, type of employment, employment medical insurance plan (including medication coverage), employment dental insurance plan, health descriptors (e.g., diet, exercise level, smoker/nonsmoker, medication allergies, etc.), educational history, gender, location, or other medical information associated with the user, or some combination thereof.

The digital pillbox 210 contains one or more records associated with different medications of the user. A record includes a plurality of fields associated with a particular medication. Fields may be populated with different aspects of prescription information for the medication, fill level (i.e., number of available doses) for the medication, schedule for taking the medication, prescribed off-label uses of the medication, vendor information for the medication, or some other information associated with the medication. In one embodiment, the digital pillbox 210 receives records associated with the user from the medical monitoring system 115. Fields within one or more of the records may periodically be updated by the medical monitoring system 115 and/or the third party database 120. The medication monitoring module 140 may automatically synchronize the records with the records in the medical monitoring system 115, etc. In some embodiments, one or more records are synchronized between the digital pillbox 210 and the medical monitoring system 115 when a user creates, modifies, or deletes one or more fields in a record and/or a record. For example, the user may add one or more records to the digital pillbox 210, and the added records are then automatically uploaded to the medical monitoring system 115. Additionally, the digital pillbox 210 includes a medication schedule that is associated with one or more of the records. The medication schedule includes information identifying what medications are being taken by the user, and in what time window those medications should be taken by the user. For example, a medication schedule may indicate that a user is to take a prescribed dose of Aspirin daily and a prescribed does of Azithromycin on Mondays, Wednesdays, and Fridays at 1:00 pm.

In some embodiments, the digital pillbox 210 stores standard image data, mass capture image data, physical data, or some combination thereof, that are associated with their corresponding prescription information. Standard image data is one or more high quality images of a medication. A high quality image is generally a high resolution image that has low noise. For example, the standard image data may be a structured product label image, a national library of medicine image, an image from the medication manufacturer, or some combination thereof. Mass capture image data are images of medications that have been extracted from images received by the medical monitoring system 115 from users of the medical monitoring system 115. Generally, the images are of much lower resolution and have higher noise than the standard image data, as the camera on the client device 105 is typically going to be lower quality (e.g., less pixels, higher noise, etc.) than the quality of the professional imaging systems used to create standard image data. Physical data relates to the physical characteristics of a medication. Physical data can include, size of the medication, color of the medication, shape of the medication, imprint or text of the medication, form of the medication (e.g., compressed tablet, capsule, powder, etc.), or some combination thereof. In some embodiments, the digital pillbox 210 may obtain standard image data and/or physical data from the third party database 120 and/or the medical monitoring system 115 separate from, or as part of prescription information.

In some embodiments, the content of one or more fields are not editable by the user. For example, warnings or interaction effects, names, descriptions and other data which a user would not generally edit (as opposed to a fill level associated with the medication) that have been retrieved from the third party database 120 and/or the medical monitoring system 115 may not be editable by the user. In some embodiments, one or more of the fields are editable. The editable fields allow a user to edit their content. For example, the fill level associated with a medication may be editable by the user.

The image processing module 215 receives images of one or more pills, such as those taken by a user with the camera 125 of the client device 105. In some embodiments, the module 215 determines whether received images are adequate for medication identification. An image of one or more medications on an uncontrolled background is adequate for medication identification if each image parameter meets certain thresholds. Image parameters include background, focus, lighting, and fill of the target area for one or more medications in the received images.

If none of the received images are adequate, the image processing module 215 can instruct the user interface module 240 to prompt the user to take one or more additional images. In some embodiments, the instruction also specifies one or more image parameters that should be adjusted in order to obtain an adequate image. If any of the received images are adequate, the image processing module 205 is configured to proceed with the identification process. In some embodiments, this means providing the images to the medical monitoring system 115, which performs the identification, including extracting certain characteristic information from the one or more medications for analysis. In other embodiments, some or all of the extraction of characteristic information occurs at the client device 105, and what is sent to the medical monitoring system 115 for the identification is the characteristic information extracted at the client device 105, and possibly also the images taken at the client device 105. In addition, the medical monitoring system 115 might perform additional extraction of characteristic information that is used by the system 115 in identifying the one or more medications along with what is sent by the client device 105. In further embodiments, the extraction and identification both occur at the client device 105, possibly in conjunction with information received from the medical monitoring system 115 (e.g., pill ID information stored in a database, reference pill images, etc.).

In some embodiments, the image processing module 215 provides one or more of the adequate images to the medication identification module 220 of the client device. Additionally, in embodiments where at least some characteristic information extraction occurs at the client device, the image processing module 215 performs this extraction. Characteristic information is information that may be used to identify the medication. For example, characteristic information may include the shape of the medication, the size of the medication, the color of the medication, any imprint on the medication, or some combination thereof. The image processing module 215 may use digital recognition and optical character recognition algorithms to identify one or more medications in an adequate image. In some embodiments, digital recognition algorithms include GRABCUT from MICROSOFT® RESEARCH. The image processing module 215 determines one or more portions of the adequate image that correspond to one or more unidentified medications. The image processing module 215 then extracts characteristic information from each of the portions of the image corresponding to the one or more unidentified medications. In some embodiments, size of a medication may be determined using one or more size references. A size reference is an object having a known size. A size reference may be, for example, common household items, coins (e.g., quarter, nickel, dime, etc), an identified medication, a pill bottle cap, etc. The image processing module 215 may utilize one or more size references to determine the relative sizes of other medications in the image. Additionally, in some embodiments, the image processing module 215 may extract depth information associated with one or more medications in the image. The depth information may then be used to determine the size of the medication and other medications in the image. Additionally, in some embodiments, the image processing module 215 may extract characteristic information associated with one or more adequate images using standard image data, mass capture image data, physical data, or some combination thereof, as described below in the context of.

The image processing module 215 is configured to provide any extracted characteristic information to the medication identification module 220.

The medication identification module 220 facilitates the determining of identification information for medications in an adequate image. In some embodiments, the medication identification module 220 is configured to generate a client request to identify one or more medications in the received one or more adequate images. The generated client request may include: one or more adequate images, any characteristic information that may have been extracted at the client device 105, an identification request type, or some combination thereof. The medication identification module 220 provides the client request to the medical monitoring system 115 (e.g., via the server interaction module 130). The medication identification module 220 receives from the medical monitoring system 115 prescription information. In embodiments, where incomplete prescription information is received, the medication identification module 220 may be configured to request the missing information from the third party database 120. In embodiments, where no prescription information is received for one or more of the pills, the medication identification module 220 may instruct the user interface module 240 to prompt the user to manually create records for the un-identified medications.

In some embodiments, the medication identification module 220 may use characteristic information received from the image processing module 215 to identify any medications in the one or more adequate images that have corresponding records in the digital pillbox 210. The medication identification module 220 may compare the characteristic information with corresponding fields in the records of the digital pillbox 210. If a match occurs, the medication identification module 220 may instruct the user interface module 240 to display identification information for the matched medications to the user. If no match occurs, the medication identification module 220 may generate a client request including the characteristic information and provide the client request to the medical monitoring system 115. Additionally, in some embodiments, if not match occurs, the medication identification module 220 may populate the prescription information with an image of the medication (e.g., extracted from the adequate image) and/or provide the extracted image to the medical monitoring system 115. In other embodiments, the medication identification module 220 provides the digital pillbox 210 information to the medical monitoring system 115 for performing the match or otherwise requests that the system 115 perform a match based on information the system 115 may have stored regarding the digital pillbox 210 for the user.

The medication identification module 220 may receive feedback from the user whether one or more of the medications in the image have been were correctly identified. In some embodiments, the medication identification module 220 may perform a machine learning algorithm using the received feedback, the image of the one or more medications, the associated characteristic information, or some combination thereof. For example, the characteristic information, the image, the feedback, or some combination thereof, can be considered input signals that are analyzed by the machine learning algorithm. The machine learning algorithm can be trained on a set of signals associated with various medications. Once the machine learning algorithm has been trained on a known data set, the algorithm can be used for determining characteristic information extraction from an image and/or what characteristic information should be associated with particular medications. The medication identification module 220 is configured to instruct the image processing module 215 to make adjustments in characteristic information in accordance with the machine learning algorithm.

The medication tracking module 225 maintains a medication schedule associated with the user that is stored in the digital pillbox 210. When a particular time window for a medication is reached, the medication tracking module 225 instructs the alert module 235 to generate an alert notifying the user that it is time to consume a dose of the medication.

In some embodiments, medication tracking module 225 is configured to log one or more medications as being consumed. The medication tracking module 225 receives from the medication identification module 220 prescription information including identification information (e.g., brand name, generic name, picture, description, or some combination thereof) for one or more of the medications in an adequate image. The medication tracking module 225 then updates the medication schedule to reflect consumption of the identified medications. Additionally, the medication tracking module 225 updates the fill level associated with each of the consumed medications in the digital pillbox 210.

The interaction effects module 230 is configured to determine interaction effects between one or more medications. The interactions effects module 230 receives from the medication identification module 220 prescription information associated with one or more of identified medications. In one embodiment, the interaction effects module 230 extracts possible interaction information from the warnings and adverse reactions sections of the prescription information for an identified medication. The interaction effects module 230 extracts identification information for medications identified in the warnings and adverse reactions section. The interaction effects module 230 is configured to compare the extracted identification information to the prescription information received from the medication identification module 220, the records in the digital pillbox 210, or both. A match indicates that interaction effects can occur between two or more of the medications. For example, prescription information for VIAGRA® (i.e., sildenafil) indicates that it should not be taken with NITREK® (nitroglycerin), and vice versa, as these drugs taken together have adverse side effects (i.e., may cause blood pressure to fall excessively, fainting, etc.). In some embodiments, the interaction effects module 230 compiles a list of any medication determined to have an interaction effect and provides it to the user (e.g., via the user interface module 240). In some embodiments, the list may include indicators indicating the severity of the interaction between medications. For example, an indicator for a serious interaction (i.e., warnings) may be identified with a red exclamation point, stop sign, etc., near the flagged medication and/or some of the text of the medication may be altered (e.g. different color, bolded, italicized, or otherwise emphasized). In contrast other interaction effects that are not warnings, may be indicated with some other indicator, e.g., a yellow exclamation point, or some other marker and/or some of the text of the medication may be altered.

Additionally, in some embodiments, the interaction effects module 230 is configured to request from the medical monitoring system 115 an image of one or more medications that is augmented with interaction information. An augmented view of an image is the image overlaid with a pictorial representation of the interaction effects between medications depicted in the image. The pictorial representation of the interaction effects may be, for example, one or more interaction lines that are displayed in the image and connect medications shown in the image that have interaction effects. An interaction line may the severity of the interaction effect. For example, a red line may indicate a serious interaction (i.e., warnings), and a yellow line may indicate less serious interaction (i.e., not warnings). Additionally, in some embodiments, an interaction line may have an associated indicator that indicates the severity of the interaction effect. Thus, multiple pills can be captured in a single image, and the interaction effects between all of the pills can be easily displayed to the user through this augmented view providing interaction connection lines between the pills.

The alert module 235 generates alerts using information in the digital pillbox 210. Alerts are notifications presented to the user that are associated with medications associated with records in the digital pillbox 210. In some embodiments, the alert module 235 may receive instructions from the medication tracking module 225 to generate an alert prompting the user to take a particular medication. In some embodiments, the alert module 235 may receive instructions from the medical monitoring system 115 to generate an alert that notifies the user of interactions information for one or more medications. In some embodiments, the alert module 235 is configured to generate an alert that prescription information associated with a medication associated with the digital pillbox 210 has been updated. In some embodiments, the alert module 235 is configured to generate an alert that a fill level of a medication associated with a user has a number of doses that is below a particular threshold. Additionally, in some embodiments, the alert module 235 is configured to generate an alert that a medication associated with the user's digital pillbox 210 has gone on sale at one or more vendors. Similarly, in some embodiments, the alert module 235 is configured to generate an alert that a medication associated with the user's digital pillbox 210 is available at one or more vendors cheaper (e.g., cost/pill) than other vendors (e.g., pharmacy closest to the user, pharmacy the user typically users, etc.). The alert module 235 is configured to present the generated alerts to the user, via the user interface module 240.

The user interface module 240 presents one or more graphical user interfaces to the user of the client device 105. The graphical user interfaces allow a user to interact with the medication monitoring module 140 and medical monitoring system 115. Additionally, the graphical user interfaces are used to present alerts to the user. In one embodiment, the user interface module 240 may present to the user one or more options for selection. Options may include, for example, a pill box option, an identify medication option, a medication interaction option, a medication log option, a profile option, an information option, a questions option, or some combination thereof, via one or more graphical user interfaces. For example, in one embodiment, the user interface module 240 presents a homepage to the user including one or more options for selection.

In some, embodiments, if the pillbox option is selected, the user interface module 240 is configured to retrieve one or more records associated with the user from the digital pillbox 210. The user interface module 240 is configured to present one or more of the retrieved records to the user. Portions of retrieved records may be presented, and the user interface module 240 may be configured to receive selections from the user to display additional information from a displayed portion of retrieved record. Additionally, the user interface module 240 may allow a user to scroll through prescription information associated with a medication. Additionally, the user interface module 240 may present different portions of prescription information in the same display to the user. For example, the user interface module 240 may present a name and image of the medication in conjunction interaction information for that medication. In some embodiments, the user interface module 240 may include an option to directly reference a portion of the prescription information as shown in the package insert, thus, allowing a user to immediately locate the relevant portion of the package insert, as opposed to manually scrolling through the package insert to locate the relevant portion.

In some embodiments, the user interface module 240 is configured to receive information from the user to create, modify, or delete, a record in the digital pillbox 210. The user interface module 240 may be configured to allow a user to add, modify, or delete one or more editable fields associated with displayed records. For example, a user may manually adjust a fill level associated with a medication.

In some embodiments, if the identify medication option is selected, the user interface module 240 is configured to activate the camera 125 and present to the user a graphical user interface showing an image area being actively captured by the camera 125. The image area may include a target area that is smaller than the image area. Additionally, the graphical user interface may present an image area to the user that includes one or more messages to help facilitate the user capturing an image adequate for medication identification given an uncontrolled background. For example, the graphical user interface may present textual messages like, hold still, increase lighting, change background, etc. In some embodiments, the user interface module 240 may prompt the user to position one or more medications such that they fall within the target area being captured by the camera 125. In some embodiments, the images actively being captured are sent to the image processing module 215 to determine whether an adequate image of the one or more medications has been taken. In other embodiments, the user positions the one or more medications in the target area and then selects an option that instructs the camera 125 to capture a single image. The single image 125 is then sent to the image processing module 215 to determine if the captured image is adequate. In some embodiments, if the image is not adequate the medication identification module 220 instructs the user interface module 125 to prompt the user to adjust one or more image parameters and re-take the image. The user interface module 240 is configured to present some or all of the prescription information received from the medication identification module 220 and/or the digital pillbox 210.

In some embodiments, the user interface module 240 is configured to prompt the user to confirm that the prescription information being presented to the user corresponds to the one or more medications in the image. For example, the user interface module 240 may present a listing of images and names of the medication which were received (as part of the prescription information) from the medication identification module 220 and/or the digital pillbox 210, and prompt the user to confirm that the listing includes any of the medications in the image. The user interface module 240 provides the feedback from the user to the medication identification module and/or the medical monitoring system 115. The feedback indicates whether the medications were identified correctly or incorrectly by the medical monitoring system 115 and/or the client device 105.

In some embodiments, if the medication interaction option is selected, the user interface module 240 is configured to automatically execute the medication identification option. The user interface module 240 is configured to present a listing of interaction information for one or more medications. In some embodiments, the user interface module 240 is configured to present an augmented reality option, which allows the user to request that interaction information be presented to the user via an augmented view. If selected, the user interface module 240 requests the augmented view from the interaction effects module 230. The interface module 205 is configured to present the augmented view to the user after is has been received from the interaction effects module 230.

In some embodiments, if the medication log option is selected, the user interface module 240 presents a graphical user interface to the user prompting them to identify which medication is being consumed, and how much of that medication is being consumed (e.g., 2×50 mg pills). For example, the graphical user interface could present a listing of records in the digital pillbox 210 for the user to select from. After selecting a record, the graphical user interface may present a window allowing the user to choose the dosage being consumed. The user may indicate the consumed dosage via, e.g., manually entering a value, an adjustable dial with different dosage values, drop down menus, may be automatically populated with the suggested dosage in record, etc.

Additionally, in some embodiments, if a medication log option is selected, the user interface module 240 is configured to execute the medication identification option described above. Additionally, the user interface module 240 notifies the medication tracking module 225 that the user wants to log the consumption of medication identified in the image of one or more medications. The user interface module 240 is configured to prompt the user to confirm that the identified medications are correct, and upon receiving affirmation, notify the medication tracking module 225 to log the consumption of the one or more medications identified in the image.

In some embodiments, if the information option is selected, the user interface module 240 retrieves information from the digital pillbox 210, the user profile store 205, the medical monitoring system 115, or some combination thereof, for presentation to the user. The user interface module 240 is configured to present personalized information about the health of the requesting user. For example, for a particular medication, given a user's age and gender, the user interface module 240 may calculate and/or retrieve from the medical monitoring system 115 an optimal time to take the medication. The user interface module 240 may present the optimal time to take the pill to the user.

In some embodiments, if the profile option is selected, the user interface module 240 retrieves information from the user profiles from the user profile store 205. The user interface module 240 is configured to present some or all of the retrieved user profile information to the user. For example, the interface module 205 may be configured to present the user's name, address, health insurance plan, etc. The user interface module 240 is configured to allow the user to update some or all of the retrieved user profile information.

In some embodiments, the questions option, if selected, presents to the user a one or more common questions about the medication and answers to those questions. Common questions may address, for example, how the medication makes a user feel, how long to take effect, is the medication dangerous, how the medication works, how the medication works with a specific population (e.g., pregnant women), etc.

Figures 3A, 3B:
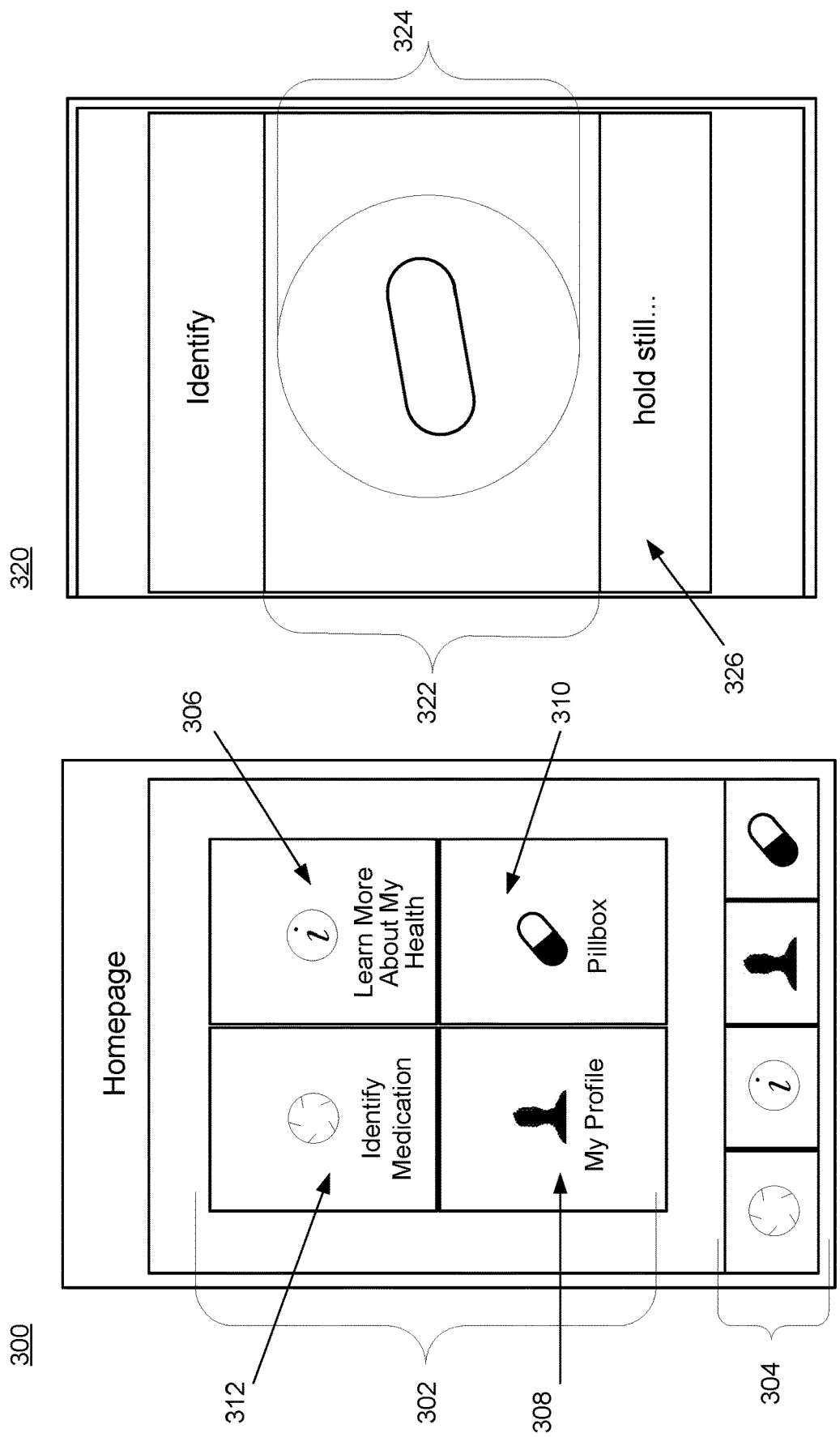
FIG. 3A illustrates an example of a user interface displayed by a client device showing a medication identification homepage according to an embodiment.
FIG. 3B illustrates an example of a user interface displayed by a client device showing a medication image capture display according to an embodiment.

FIG. 3A illustrates an example of a user interface 300 displayed by the client device 105 showing a medication identification homepage according to an embodiment. The user interface 300 includes a main menu 302 and a submenu 304. The main menu 302 displays various options to the user for selection. For example, an information option 306, a profile option 308, a pillbox option 310, and an identify medication option 312. The submenu 304 may display the same or different options as the main menu 302. In embodiments not shown the main menu 302 and/or the submenu 304 may display other options as well. For example, the main menu 302 and/or the submenu 304 may display a medication interaction option, a medication log option, etc.

FIG. 3B illustrates an example of a user interface 320 displayed by the client device 105 showing a medication image capture display according to an embodiment. The user interface 320 displays an image area 322, a target area 324, and a message area 326.

Figures 3C, 3D:
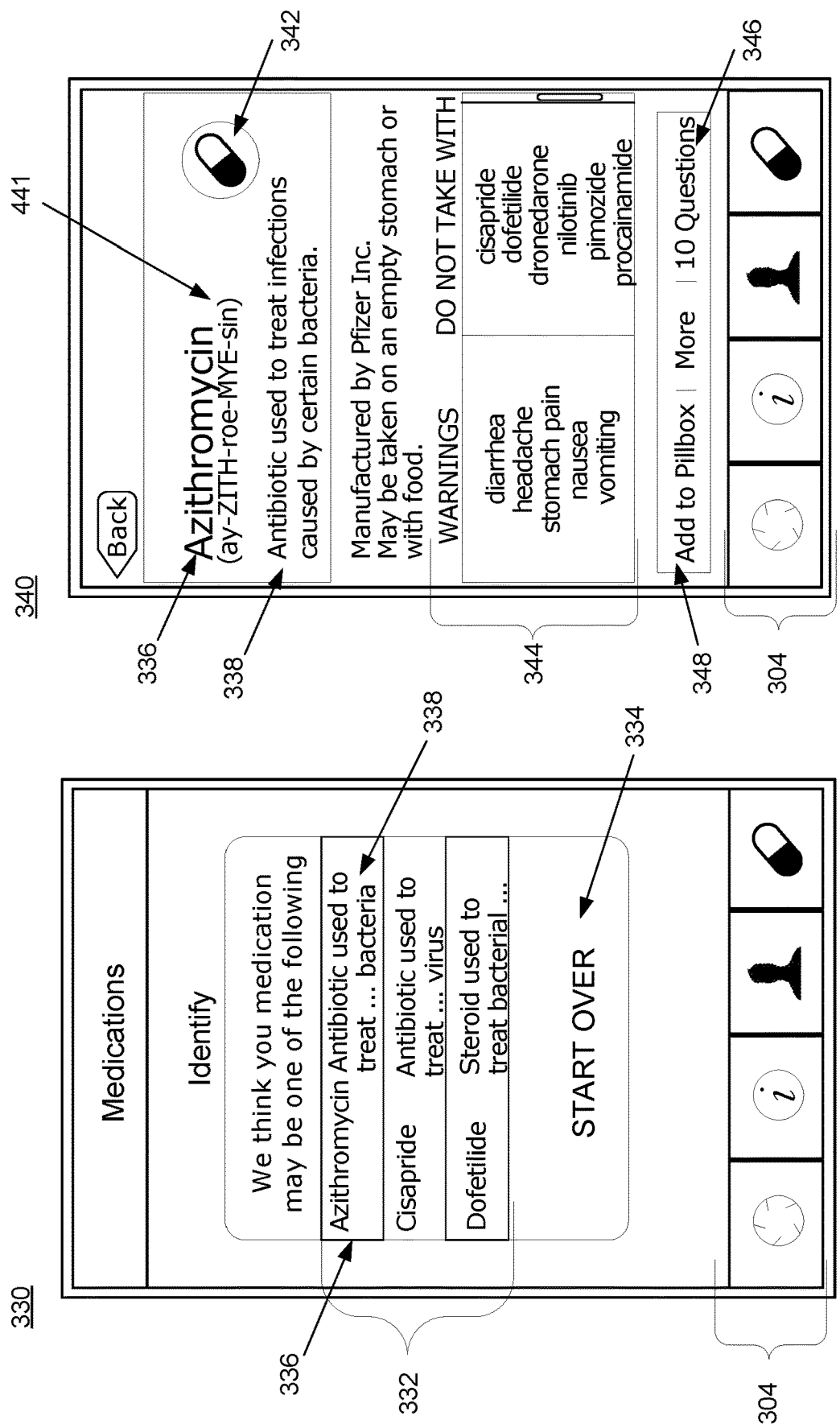
FIG. 3C illustrates an example of a user interface displayed by a client device listing possible identification information for an unidentified medication according to an embodiment.
FIG. 3D illustrates an example of a user interface displayed by a client device listing prescription information for a medication according to an embodiment.

FIG. 3C illustrates an example of a user interface 330 displayed by the client device 105 listing possible identification information for an unidentified medication according to an embodiment. The user interface 330 displays a listing 332 of one or more medications that may correspond to a captured image of an unidentified medication, and an option 334 to try the medication identification process again. The user interface 330 displays a portion of the prescription information for each of the medications displayed in the listing 332. For example, the user interface 330 may display a name 336 and a description 338 for each of the listed medications. In embodiments, not shown, the user interface 330 may also display an image of the medication for one or more of the medications in the listing 332.

FIG. 3D illustrates an example of a user interface 340 displayed by the client device 105 listing prescription information for a medication according to an embodiment. The user interface 340 displays the name 336, the description 338, pronunciation information 441, and an image of the medication 342. The user interface 340 also displays other prescription information associated with medication. For example, the user interface 340 displays the manufacturer of the medication, conditions for taking the medication (e.g., with food), and interaction information 344 associated with the medication. The user interface 340 also displays a questions option 346 and an 'add to pillbox' option 348. The add to pillbox option 346, allows the user to indicated a desire to add the described medication to their digital pillbox 210.

Figures 3E, 3F:
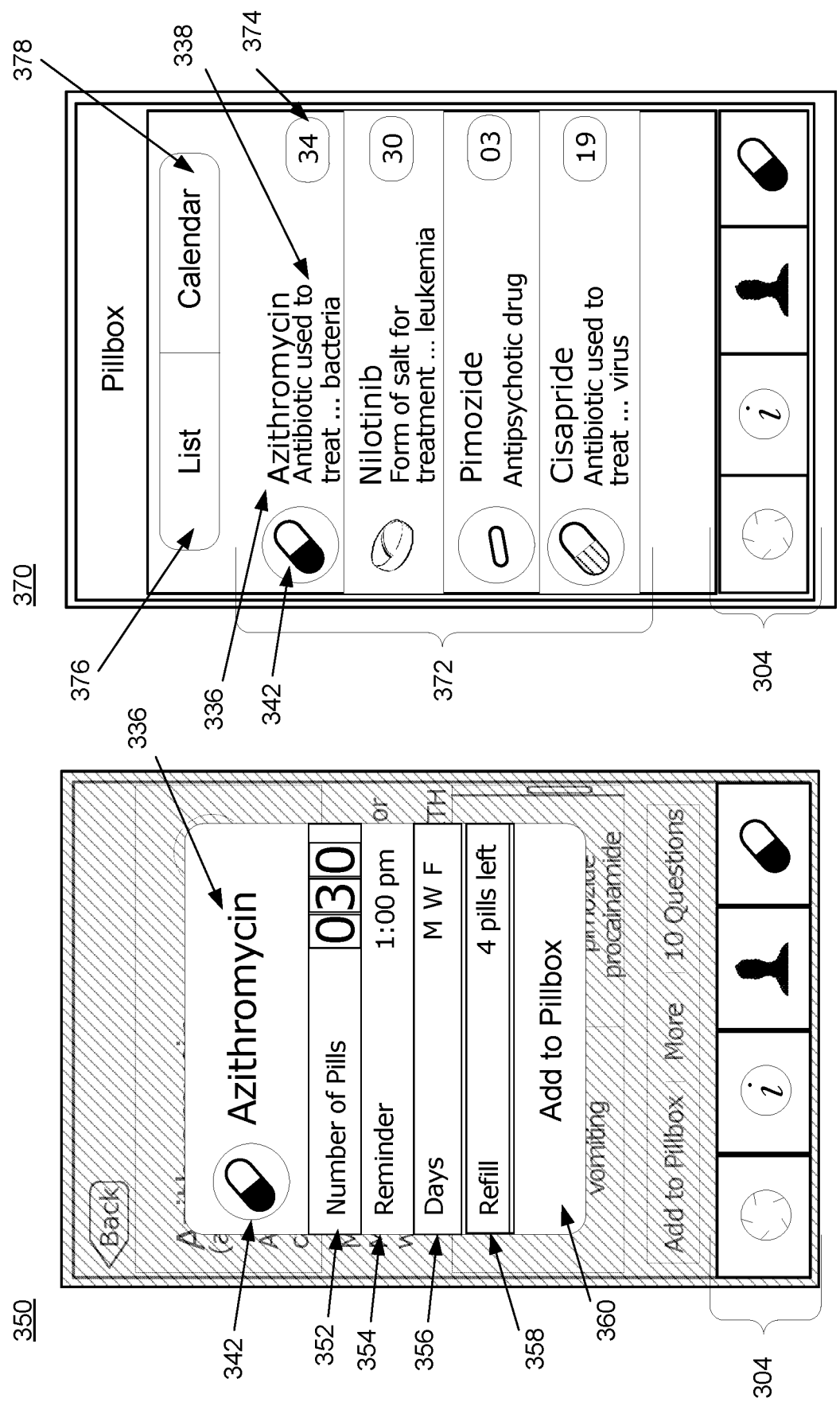
FIG. 3E illustrates an example of a user interface displayed by a client device after an add to pillbox option is selected according to an embodiment.
FIG. 3F illustrates an example of a user interface displaying prescription information from a digital pillbox according to an embodiment.

FIG. 3E illustrates an example of a user interface 350 displayed by the client device 105 after an add to pillbox option is selected according to an embodiment. The user interface 350 displays the name 336 and image 342 of the medication, a number of pills to be added field 352, a reminder field 354, a schedule field 356, a fill level field 358, and an add softbutton 360. The user interface 350 allows the user to edit one or more of the fields 352, 354, 356, and 358. In this example, the user is adding 30 additional Azithromycin pills to the 4 remaining Azithromycin pills already associated with the user's digital pillbox 210. In other embodiments, this may be a medication that is not already in the user's digital pillbox 210. If selected, the add softbutton 360 updates the user's digital pillbox 210 with the prescription information associated with the medication being added.

FIG. 3F illustrates an example of a user interface 370 displaying prescription information from a digital pillbox 210 according to an embodiment. The user interface 370 presents a listing 372 of medications associated with the digital pillbox 210. In this embodiment, the listing includes the names, the descriptions, the images, and fill level for each of the medications. In this example, the fill level 374 of Azithromycin is 34 pills because as discussed above in FIG. 3E the user added 30 pills to 4 pills of the previous fill level. The user interface 370 also includes a list softbutton 376 and a calendar softbutton 378. If the list softbutton 376 is selected, some of the prescription information associated with each medication is displayed to the user. In this example, the list softbutton 376 has been selected. If the calendar softbutton 378 is selected, the user interface 370 displays a calendar that depicts when the user should take the medications in the digital pillbox 210.

Medical Monitoring System

Figure 4:
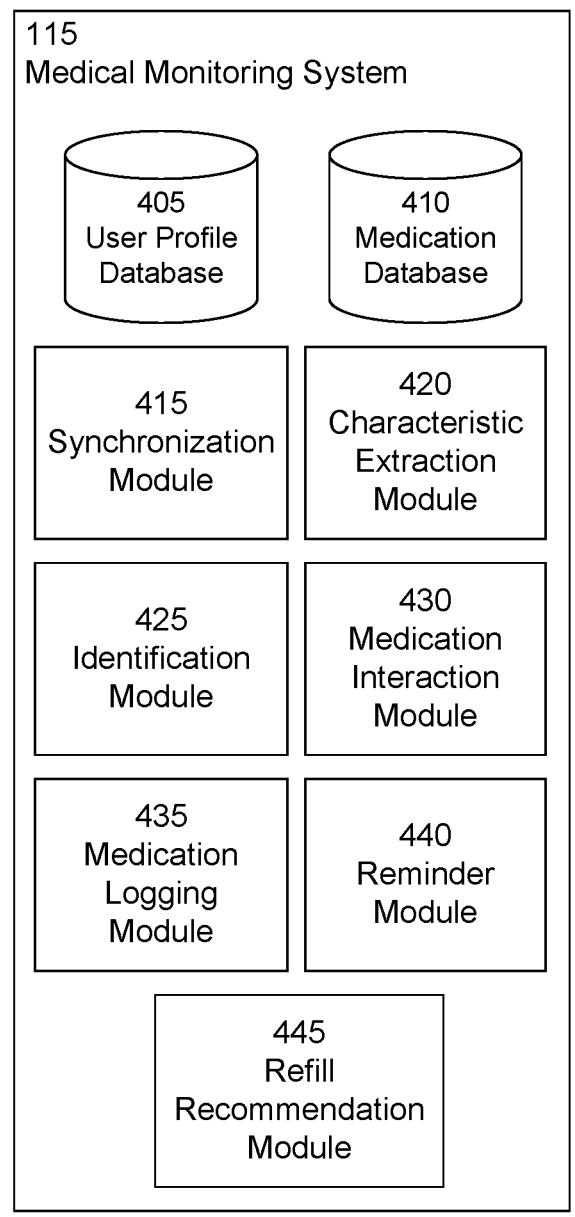
FIG. 4 is a high level block diagram illustrating a detailed view of a medical monitoring system according to one embodiment.

FIG. 4 is a high-level block diagram illustrating a detailed view of the medical monitoring system 115 according to one embodiment. The medical monitoring system 115 is comprised of modules including a user profile store 405, a medication database 410, a synchronization module 415, a characteristic extraction module 420, an identification module 425, a medication interaction module 430, a medication logging module 435, a reminder module 440, and a refill recommendation module 445. Some embodiments of the medical monitoring system 115 have different modules than those described here. Similarly, the functions can be distributed among the modules in a different manner than is described here.

In some embodiments, each user of the medical monitoring system 115 can be associated with a user profile, which is stored in the user profile database 405. Additionally, each user profile stored in the user profile database 405 includes the same information that is in the digital pillbox associated with that user. Thus, the medical monitoring system 115 is able to monitor what information (e.g., prescription information, medication schedule, etc.) a user has stored in their digital pillbox on a user-by-user basis. In some embodiments, some or all of the information that is in the digital pillboxes associated with users of the medical monitoring system 115 may be aggregated. The aggregated information may be used to determine high level trend data and personalized recommendations back to the user.

The medication database 410 stores prescription information associated with different medications. The medication database 410 may update its prescription information based on changes to prescription information in, for example, the third party database 120 and/or manual updates received from an administrator. Additionally, the medication database 410 stores standard image data, mass capture image data, physical data, or some combination thereof that are associated with their corresponding prescription information. In some embodiments, when an adequate image received from a client device 105 is successfully used to identify a medication (i.e., user confirms that identification was correct) the medication database 410 automatically stores and associates the adequate image with the identified medication. In some embodiments, the medication database 410 may obtain standard image data and/or physical data from the third party database 120, separate from, or as part of prescription information.

The synchronization module 415 synchronizes the prescription information stored in the medication database 410 with prescription information in the third party database 120. If a change occurs to prescription information for a medication at the third party database 120, the synchronization module 415 automatically updates the medication database 410 with the change. For example, if a new medication is added to the third party database 120, the synchronization module 415 automatically detects the newly added content, and updates the medication database 410 with prescription information associated with the new medication. Similarly, if prescription information for a particular medication is modified (e.g., add additional adverse effect) the synchronization module 310 automatically detects the change and modifies the corresponding prescription information in the medication database 410 accordingly.

Additionally, the synchronization module 415 synchronizes the prescription information stored in the medication database 410 with the prescription information in user's digital pillboxes 210 and/or the user profile database 405. Changes made to the prescription information at the third party database 120 are automatically made to information associated with user profiles including prescription information associated with the same medication. Additionally, the changed prescription information may be pushed to digital pillboxes 210 that contain the corresponding prescription information. For example, if an interaction effect is added to Aspirin at the third party database 120, the synchronization module 415 may automatically update corresponding prescription information for Aspirin in the user profile database 405, and push the changes to any digital pillbox 210 that includes prescription information for Aspirin. Additionally, in cases where a record associated with a medication not in the medication database 410 are received from a client device 105, the synchronization module 415 updates the medication database 410 with the new record.

The characteristic extraction module 420 extracts some characteristic information from an adequate image received from a client device 105. The characteristic information is extracted in the same manner as discussed above with reference to the image processing module 215. Additionally, the characteristic extraction module 420 may extract characteristic information associated with one or more adequate images using standard image data, mass capture image data, physical data, or some combination thereof. The characteristic extraction module 420 is configured to provide any extracted characteristic information to the identification module 425.

The identification module 425 uses characteristic information received from the characteristic extraction module 420 to identify any medications in the adequate image using the medication database 410 and/or the third party database 120. The identification module 425 may compare the characteristic information with the prescription information stored in the medication database 410 and/or the third party database 120. If a match occurs, the identification module 425 retrieves the matching prescription information and provides it to the client device 105. If no match occurs, the identification module 425 notifies the client device 105 that no matching prescription information is available. Additionally, in some embodiments, if the prescription information in the medication database 410 does not include an image of the medication, the identification module 425 may populate the prescription information with an image of the medication (e.g., extracted from the adequate image received from a client device 105).

The identification module 425 may receive feedback information from various users of the client devices 105 regarding whether medications in images were correctly identified. In some embodiments, the identification module 425 may perform a machine learning algorithm using the received feedback from the plurality of client devices 105, the image of the one or more medications, the associated characteristic information, or some combination thereof. For example, the characteristic information, the image, the feedback, or some combination thereof, can be considered input signals and analyzed by the machine learning algorithm. The machine learning algorithm can be trained on a set of signals associated with various medications. Once the machine learning algorithm has been trained on a known data set, the algorithm can be used for determining characteristic information extraction from an image and/or what characteristic information should be associated with particular medications. The identification module 425 is configured to instruct the characteristic extraction module 420 to make adjustments in characteristic information in accordance with the machine learning algorithm.

The medication interaction module 430 is configured to determine interaction effects between one or more medications. The medication interaction module 430 receives from the identification module 425 prescription information associated with one or more of identified medications. In some embodiments, the medication interaction module 430 extracts possible interaction information from the warnings and adverse reactions sections of the received prescription information for an identified medication. The medication interaction module 430 extracts identification information for medications identified in the warnings and adverse reactions sections of the prescription information. The medication interaction module 430 is configured to compare the extracted identification information to the other received prescription information, the records in the medication database 410 associated with the user, or both. A match indicates that interaction effects can occur between two or more of the medications. The medication interaction module 430 generates a list of any medication determined to have an interaction effect in the same manner discussed above with reference to the interaction effects module 230.

Additionally, in some embodiments, the medication interaction module 430 is configured to generate an augmented view of a received adequate image of one or more medications. The medication interaction module 430 is configured to provide the generated list and/or an augmented view of an adequate image to the client device 105.

The medication logging module 435 maintains a medication schedule for each of a plurality of users of the medical monitoring system 115. In some embodiments, when a particular time window for a medication is reached, the medication logging module 435 may instruct the client device 105 to generate an alert notifying the user that it is time to consume a dose of the medication. This option may be enabled or disabled by each user. Additionally, in some embodiments, the medication logging module 435 is configured to log one or more medications as being consumed by users of the medical monitoring system 115. The medication logging module 435 receives from the identification module 425 prescription information including identification information (e.g., brand name, generic name, picture, or some combination thereof) for one or more of the medications in a client request from a user. The medication logging module 435 then updates a medication schedule associated with the user to reflect consumption of the identified medications, updates the fill level associated with each of the consumed medications in the digital pillbox 210, or both.

In some embodiments, if the medication logging module 435 does not receive a client request to log the consumption of a medication within the time window, the medication logging module 435 may instruct the reminder module 440 to provide the user with one or more alerts. The reminder module 440 generates alerts or instructions to provide an alert to one or more client devices 105 associated with users of the medical monitoring system 115. In some embodiments, the reminder module 440 may receive instructions from the medication logging module 435 to instruct the client device 105 to generate an alert (and/or instruct a client device to generate an alert) prompting the user to take a particular medication, informing the user to a change in prescription information, providing interaction effect information, or some other communication relevant to one or more medications association with the user. If the client 105, is non responsive (e.g., turned off), the reminder module 440 may send an alert to the user via a different communication pathway. Different communication pathways include, e.g., calling one or more phone numbers in their user profile, texting, emailing, etc. In some embodiments, the reminder module 440 may receive instructions from the refill recommendation module 445 to instruct the client device 105 to generate an alert (and/or instruct a client device to generate an alert) informing the user a medication associated with the user's digital pillbox has gone on sale at one or more vendors, that a medication associated with the user's digital pillbox is available at one or more vendors cheaper (e.g., cost/pill) than other vendors (e.g., pharmacy closest to the user, pharmacy the user typically users, etc.), a medication associated with a user has a number of doses that is below a particular threshold, to inform the user to some other aspect of vendor information (e.g., a medication is now available at a particular vendor), or some combination thereof.

The refill recommendation module 445 determines possible vendor information for one or more medications associated with each user's digital pillbox. Vendor information is information describing how a user can obtain a particular medication. Vendor information can include, e.g., location for purchase, price (and if covered by health insurance plan), suggested alternative medications (e.g., one or more generic medications as alternatives to a brand name medication currently being taken), or some combination thereof. In some embodiments, the refill recommendation module 445 receives portions of the vendor information from one or more vendors and/or third party data brokers. The refill recommendation module 445 may compare prescription information associated with the medication associated with the user with prescription information in the medication database 410 and/or the third party database 120 to identify any alternative medications. An alternative medication would be a generic corresponding to a brand name medication, or vice versa. Alternative medications can also include alternative suggestions for treating the same condition (e.g., multiple other medication options for treatment of heartburn or non-medication options, such as diet changes, exercise, massage, acupuncture, etc.) The refill recommendation module 445 may then determine location for purchase, price, etc., as described above.

In some embodiments, the refill recommendation module 445 automatically provides vendor information to the client device 105 and/or the reminder module 440 when the fill information indicates a medication associated with a user has a number of doses that is below a particular threshold. In some embodiments, the threshold is set by the user. Alternatively, the refill recommendation module 445 may automatically set the threshold such that vendor information is provided to the user a certain time (e.g., 48 hours) before the fill level associated with the medication reaches zero. Additionally, in some embodiments, the refill recommendation module 445 may to provide vendor information to a client device 105 at any time. In some embodiments, the recommendation module 445 automatically orders the refill from a vendor, such as the vendor used previously in ordering refills by the system or indicated by the user, or a vendor preferred by the system.

Medication Identification on a Client Device

Figure 5:
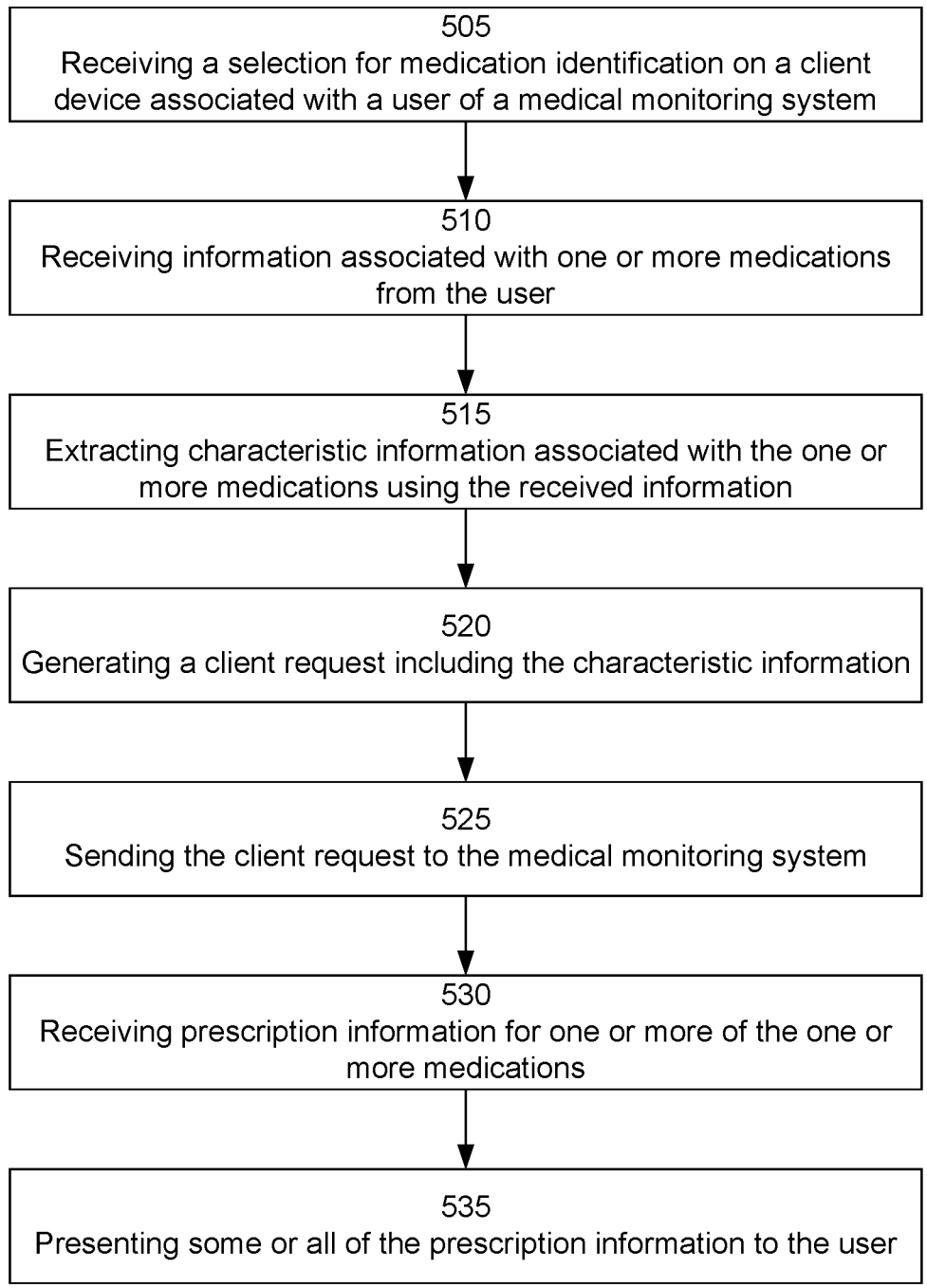
FIG. 5 is a flowchart illustrating the process of performing medication identification according to one embodiment.

FIG. 5 is a flowchart illustrating the process of performing medication identification according to one embodiment. In one embodiment, the process of FIG. 5 is performed by the client device 105. Other entities may perform some or all of the steps of the process in other embodiments. Likewise, embodiments may include different and/or additional steps, or perform the steps in different orders.

The client device 105 receives 505 a selection for medication identification from a user of a medical monitoring system 115. The user selects an option on a user interface. In some embodiments, the user interface may activate a camera 125. In other embodiments, the user interface may prompt the user to manually enter information associated with one or more medications.

The client device 105 receives 510 information associated with one or more medications from the user. In some embodiments, the client device 105 captures one or more images of one or more medications until an adequate image for medication identification has been obtained. Additionally, in some embodiments, after the client device 105 acquires an adequate image of one side of the one or more medications, the client device 105 may prompt the user to take an additional image of the opposite sides of the one or more medications. In other embodiments, the received information corresponds to textual information that describes the one or more medications. For example, color of the medication, imprint on the medication, etc.

As explained above, in some embodiments, the client device 105 extracts 515 characteristic information associated with the one or more medications using the received information. In these embodiments, the client device 105 may extract characteristic information from one or more adequate images of the medication and/or textual information received from the user. For example, the client device 105 may determine there are two pills in the adequate image, the color of each pill, the shape of each pill, the imprint on each pill, the relative size of each pill, or some combination thereof. Additionally, if there are adequate images for both sides of the one or more medications, the client device 105 may extract characteristic information for both sides of the one or more medications (e.g., where the sides may have a different imprint, color, etc.).

The client device 105 generates 520 a client request. The request can include the images to be sent to the medical monitoring system 115 for identification. The request can also include any characteristic information extraction is not performed including the characteristic information. Additionally, in some embodiments, the client request includes one or more of the adequate images. The client device 105 sends 525 the client request to the medical monitoring system 115.

The client device 105 receives 530 prescription information for one or more of the one or more medications. The received prescription information including identification information for the one or more medications. The client device 105 presents 535 some or all of the prescription information to the user. For example, the client device 105 may present a list of the identified medications that includes an image of the medication, the name of the medication, a description of the medication, some other aspect of the prescription information, or some combination thereof. In some embodiments, if no prescription information is received for one or more of the medications, the client device 105 may prompt the user to enter information known about the medication. The client device 105 may then upload this information to the medical monitoring system 115.

Alerts and Medication Tracking on a Client Device

Figure 6:
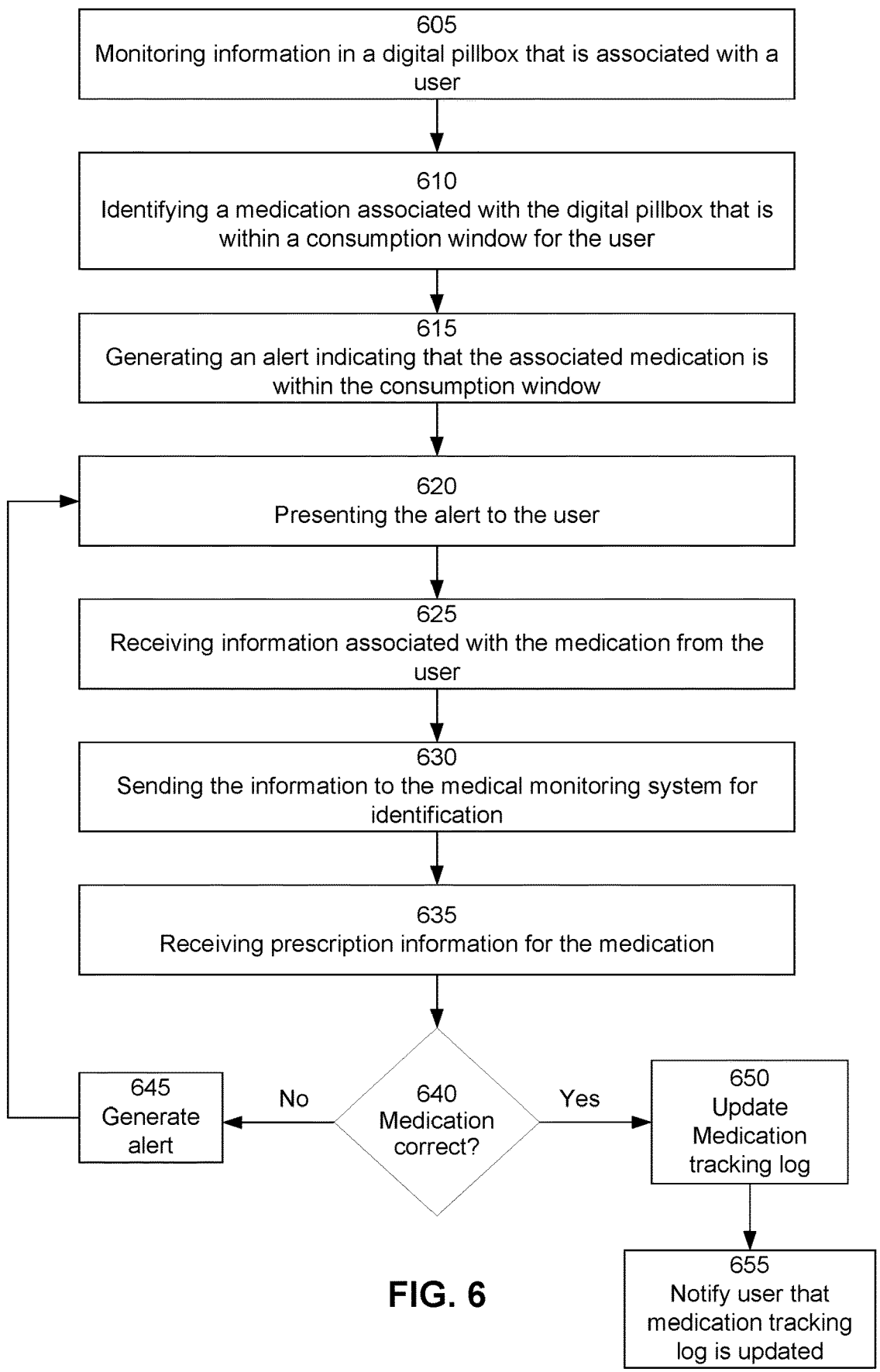
FIG. 6 is a flowchart illustrating the process of providing alerts and medication tracking for a user of a medical monitoring system according to one embodiment

FIG. 6 is a flowchart illustrating the process of providing alerts and medication tracking for a user of the medical monitoring system 115 according to one embodiment. In one embodiment, the process of FIG. 6 is performed by the client device 105. Other entities may perform some or all of the steps of the process in other embodiments. Likewise, embodiments may include different and/or additional steps, or perform the steps in different orders.

The client device 105 monitors 605 information in a digital pillbox 210 that is associated with a user. The client device 105 monitors, e.g., a medication schedule, and one or more records associated with different medications. For example, the client device 105 may monitor the fill level of one or more medications.

The client device 105 identifies 610 a medication associated with the digital pillbox 210 that is within a consumption window for the user. For example, the client device 105 can utilize the medication schedule to identify the consumption window for one or more medications associated with the digital pillbox 210. The client device 105 generates 615 an alert indicating that the associated medication is within the consumption user, and presents 620 the alert to the user. For example, the client device 105 may generate and present a pop up window indicating that it is time for the user to take a dose of Lipitor®. Additionally, in some embodiments, the alert may include an option to log consumption of the medication. Responsive to selecting the option, the client device may automatically activate a camera to enable the user to capture one or more images of the medication.

The client device 105 receives 625 information associated with the medication from the user. In some embodiments, the client device 105 captures one or more images of the medication until an adequate image for medication identification has been obtained. Additionally, in some embodiments, after the client device 105 acquires an adequate image of one side of the medication, the client device 105 may prompt the user to take an additional image of the opposite side of the medication.

The client device 105 then sends 630 the information to the medical monitoring system 115 for identification. The information is sent as part of a client request to the medical monitoring system. The client request may include one or more adequate images of the medication and/or characteristic information. The client device then receives 635 prescription information for the medication. The prescription may be received from, for example, the medical monitoring system 115 and/or the third party database 120.

The client device 105 determines 640 whether the received prescription information corresponds to the medication. If not, the imaged medication is not the medication the user is supposed to be taking, and an alert is generated 645 that notifies the user is not taking the correct medication. In some embodiments, the alert may include some prescription information from the medication that should be consumed, some prescription information for the one imaged, or some combination thereof. For example, the alert may indicate that the image medication is Lipitor® and not Oxycodone, and contain images for both medications. The process flow then proceeds to step 520 as described above.

If the medication is correct, the client device 105 updates 650 the medication tracking log to show that the medication has been consumed. Additionally, the client device 105 updates the fill level associated with the consumed medication. The client device 105 notifies 655 the user that the medication tracking log has been updated.

Medication Identification on a Medical Monitoring System

Figure 7:
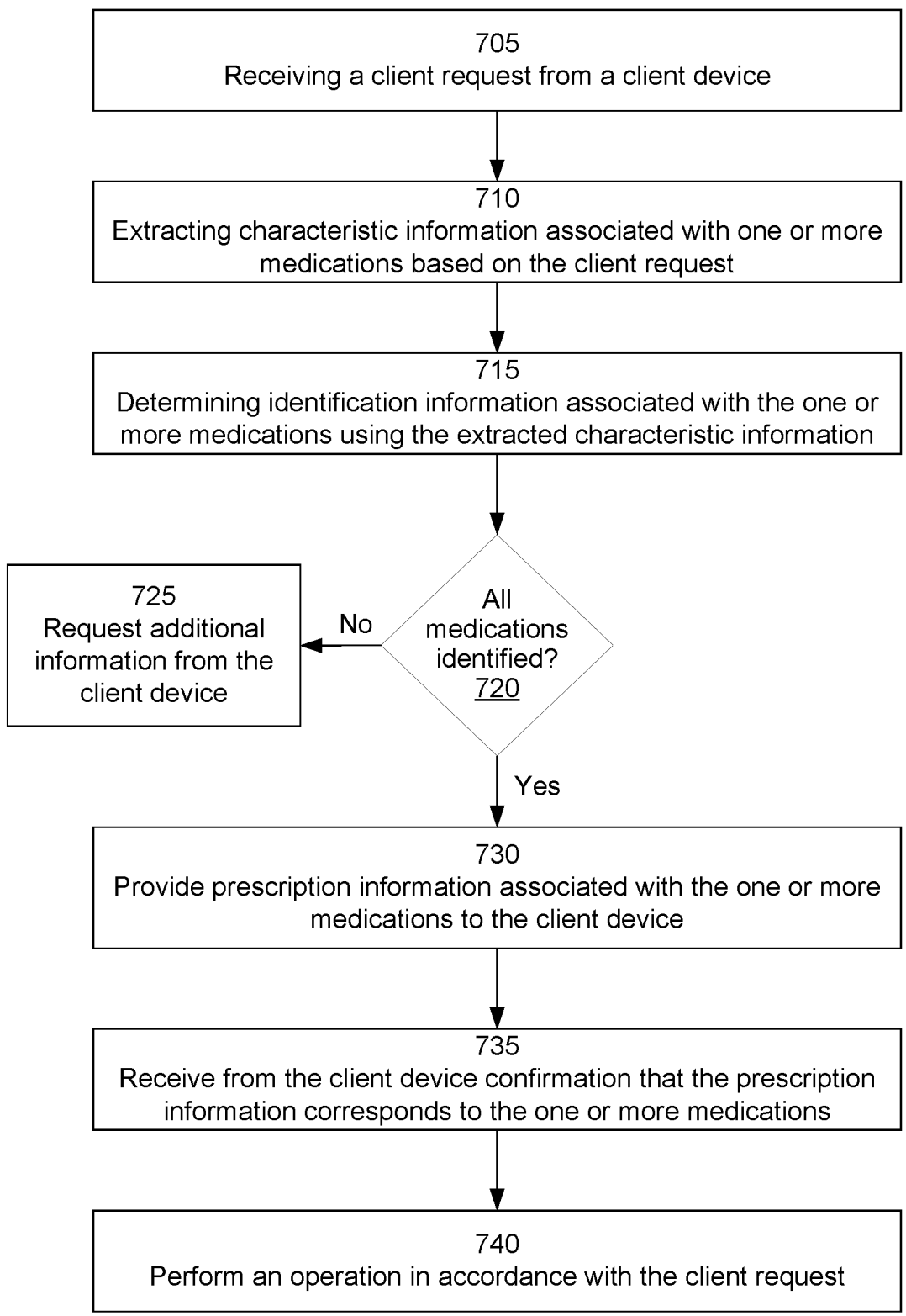
FIG. 7 is a flowchart illustrating the process of identifying one or more medications via the medical monitoring system according to one embodiment.

FIG. 7 is a flowchart illustrating the process of identifying one or more medications via the medical monitoring system 115 according to one embodiment. In one embodiment, the process of FIG. 7 is performed by the medical monitoring system 115. Other entities may perform some or all of the steps of the process in other embodiments. Likewise, embodiments may include different and/or additional steps, or perform the steps in different orders.

The medical monitoring system 115 receives 705 a client request from a client device 105. The client request may be, for example, to identify one or more medications, to log consumption of one or more medications, to request interaction effects information for one or more medications, or some combination thereof.

The medical monitoring system 115 extracts 710 characteristic information associated with one or more medications based on the client request. For example, the medical monitoring system 115 may extract characteristic information from one or more adequate images or textual information within the client request. In some embodiments, the client request can include some characteristic information, as well, that was extracted at the client device 105.

The medical monitoring system 115 determines 715 identification information associated with the one or more pills using the extracted characteristic information. For example, the medical monitoring system 115 compares the characteristic information with the prescription information stored in the medication database 410 and/or the third party database 120 to identify one or more of the one or more medications.

The medical monitoring system 115 determines 720 whether all of the medications associated with the client request have been identified. If not, the medical monitoring system 115 may request 725 additional information from the client device 105. If all of the one or more medications are identified, the medical monitoring system 115 provides 730 prescription information associated with the one or more medications to the client device 105.

The medical monitoring system 115 receives 735 from the client device 105 confirmation that the prescription information corresponds to the one or more medications.

The medical monitoring system 115 performs 740 an operation in accordance with the client request. For example, the medical monitoring system may log consumption of the one or more medications, determine interaction effects information, etc.

Determining Interaction Information on a Medical Monitoring System

Figure 8:
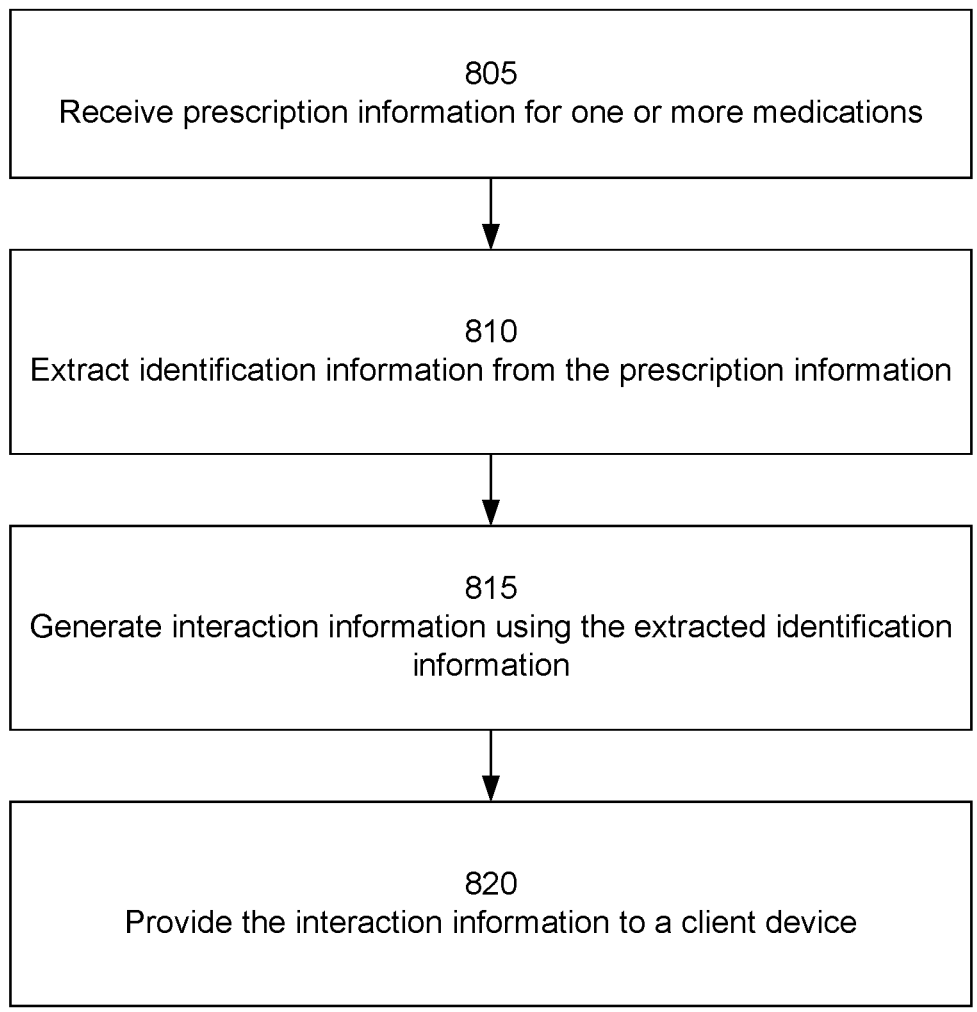
FIG. 8 is a flowchart illustrating the process of performing an operation in accordance with FIG. 7 for determining interaction information according to one embodiment.

FIG. 8 is a flowchart illustrating the process of performing an operation in accordance with FIG. 7 for determining interaction information according to one embodiment. In one embodiment, the process of FIG. 8 is performed by the medical monitoring system 115. Other entities may perform some or all of the steps of the process in other embodiments. Likewise, embodiments may include different and/or additional steps, or perform the steps in different orders.

The medical monitoring system 115 receives 805 prescription information for one or more medications. The prescription information may be associated with one or more medications identified by the medical monitoring system (e.g., as discussed above with reference to FIG. 7) and/or may be associated with one or more records in the digital pillbox of a user of the medical monitoring system 115.

The medical monitoring system 810 extracts identification information from the received prescription information. For example, the medical monitoring system may extract names of medications in the warning and/or adverse effects sections of the received prescription information.

The medical monitoring system 115 generates 815 interaction information using the extracted identification information. For example, the medical monitoring system 115 may determine whether any of the extracted identification information matches any of the prescription information for all of the one or more medications. Additionally, in embodiments, the medical monitoring system 115 may generate an augmented view of one or more adequate images used to identify the prescription information associated with the one or more medications.

The medical monitoring system 115 provides 820 the interaction information to a client device 105 associated with the user.

Determining Vendor Information on a Medical Monitoring System

Figure 9:
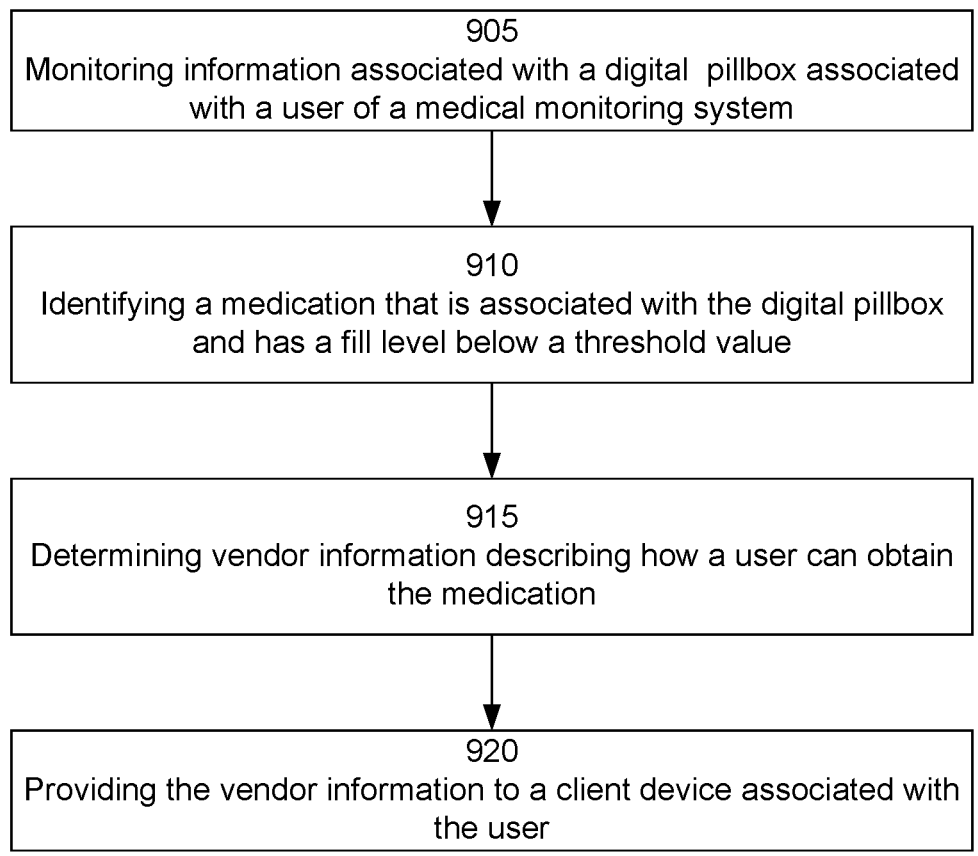
FIG. 9 is a flowchart illustrating the process of determining vendor information according to one embodiment

FIG. 9 is a flowchart illustrating the process of determining vendor information according to one embodiment. In one embodiment, the process of FIG. 9 is performed by the medical monitoring system 115. Other entities may perform some or all of the steps of the process in other embodiments. Likewise, embodiments may include different and/or additional steps, or perform the steps in different orders.

The medical monitoring system 115 monitors 905 information associated with a digital pillbox 210 that is associated with a user of the medical monitoring system 115. For example, the medical monitoring system 115 may monitor the information stored in a user profile associated with the user, the information corresponding to the digital pillbox 210 maintained on the client device 105.

The medical monitoring system 115 identifies 910 a medication that is associated with the digital pillbox 210 and has a fill level below a threshold value. The medical monitoring system 115 determines 915 vendor information describing how a user can obtain the medication. For example, the vendor information may describe one or more purchase locations, prices for the medication, suggested alternative medications (e.g., generics), etc. The medical monitoring system 115 provides 920 the vendor information to the client device 105 associated with the user.

Additional Configuration Considerations

The foregoing description of the embodiments has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method comprising:
   determining, for at least two medications in an image, prescription information using a medication database;
   determining an interaction effect between the at least two medications in the image based on the determined prescription information;
   generating a pictorial representation of the determined interaction effect that is represented as an interaction line connecting the at least two medications, the interaction line indicating a severity of the interaction effect;
   overlaying the image with the pictorial representation of the determined interaction effect to generate an augmented image of the at least two medications; and
   providing the augmented image to a mobile device.

2. The method of claim 1, further comprising:
   identifying at least two medications in the image using extracted characteristic information and an identification database, the identification database containing mappings between prescription information and associated characteristic information for a plurality of medications; and
   determining interaction information associated with the at least two medications in the image.

3. The method of claim 2, wherein the extracted characteristic information includes at least one of: medication shape, medication color, medication imprint, medication scoring, and medication size.

4. The method of claim 2, wherein the interaction information includes a warning and an adverse effect included in the prescription information for medications in the image.

5. The method of claim 1, wherein determining the interaction effect between the at least two medications in the image further comprises:
   extracting identification information for each of the at least two medications in the image from portions of prescription information associated with the medication in the image; and
   comparing the extracted identification information to the prescription information associated with each medication in the image.

6. The method of claim 5, further comprising:
   comparing the extracted identification information to the prescription information associated with one or more medications that are associated with a user profile associated with a user.

7. The method of claim 2, wherein the interaction information comprises a listing of medications that have interaction effects with one or more of the medications in the image.

8. The method of claim 1, wherein determining the interaction effect between the at least two medications in the image further comprises:
   receiving the image from the mobile device;
   determining prescription information associated with the at least two medications in the image from the medication database; and
   providing the determined prescription information to the mobile device.

9. The method of claim 1, further comprising:
   generating a list of interaction effects, wherein the list comprises indicators indicating a severity of each interaction effect of the list; and
   providing the list to the mobile device for presentation to a user.

10. The method of claim 1, further comprising:
    determining a listing of one or more vendors and a respective purchase price for each of the at least two medications in the image from each of the one or more vendors, one or more generics of each medication, or both, from a medical monitoring system; and
    providing the listing to the mobile device for presentation to a user.

11. A method comprising:
    determining, for at least two medications in an image, prescription information using a medication database;
    determining an interaction effect between the at least two medications in the image based on the determined prescription information;
    generating a pictorial representation of the determined interaction effect that is represented as an interaction line connecting the at least two medications, the interaction line indicating a severity of the interaction effect;
    overlaying the image with the pictorial representation of the determined interaction effect to generate an augmented image of the at least two medications; and
    presenting, by a display on a mobile device, the augmented image to a user of the mobile device.

12. The method of claim 11, further comprising:
    identifying at least two medications in the image using extracted characteristic information and an identification database, the identification database containing mappings between prescription information and associated characteristic information for a plurality of medications; and determining interaction information associated with the at least two medications in the image.

13. The method of claim 12, wherein the interaction information includes a warning and an adverse effect included in the prescription information for medications in the image.

14. The method of claim 11, wherein determining the interaction effect between the at least two medications in the image further comprises:
    extracting identification information for each of the at least two medications in the image from portions of prescription information associated with the medication in the image; and
    comparing the extracted identification information to the prescription information associated with each medication in the image.

15. The method of claim 12, wherein the interaction information comprises a listing of medications that have interaction effects with one or more of the medications in the image.

16. The method of claim 11, wherein determining the interaction effect between the at least two medications in the image further comprises:
    determining prescription information associated with the at least two medications in the image from the medication database; and
    presenting, by the mobile device, the determined prescription information to the user of the mobile device.

17. The method of claim 11, further comprising:
    generating a list of interaction effects, wherein the list comprises indicators indicating a severity of each interaction effect of the list; and
    presenting, by the mobile device, the list to the user of the mobile device.

18. A non-transitory computer-readable storage medium storing executable computer program instructions, the instructions executable to perform steps comprising:
    determining, for at least two medications in an image, prescription information using a medication database;
    determining an interaction effect between the at least two medications in the image based on the determined prescription information;
    generating a pictorial representation of the determined interaction effect that is represented as an interaction line connecting the at least two medications, the interaction line indicating a severity of the interaction effect;
    overlaying the image with the pictorial representation of the determined interaction effect to generate an augmented image of the at least two medications; and
    providing the augmented image to a mobile device.

19. The computer-readable medium of claim 18, further comprising:
    identifying at least two medications in the image using extracted characteristic information and an identification database, the identification database containing mappings between prescription information and associated characteristic information for a plurality of medications; and
    determining interaction information associated with the at least two medications in the image.

20. The computer-readable medium of claim 19, wherein determining the interaction effect between the at least two medications in the image further comprises:
    extracting identification information for each of the at least two medications in the image from portions of prescription information associated with the medication in the image; and
    comparing the extracted identification information to the prescription information associated with each medication in the image.

* * * * *

UNITED STATES PATENT AND TRADEMARK OFFICE
CERTIFICATE OF CORRECTION

PATENT NO. : 10,896,244 B2  Page 1 of 1
APPLICATION NO. : 16/720020
DATED : January 19, 2021
INVENTOR(S) : Mohebbi et al.

It is certified that error appears in the above-identified patent and that said Letters Patent is hereby corrected as shown below:

On the Title Page

Item (58), in Column 2, under "Field of Classification Search", Line 1, delete "None" and insert
-- USPC ............... 705/2, 3 --, therefor.

In the Claims

In Column 26, in Claim 19, Line 15, delete "medium" and insert -- storage medium --, therefor.

In Column 26, in Claim 20, Line 25, delete "medium" and insert -- storage medium --, therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*